United States Patent
Sha

(10) Patent No.: US 11,647,715 B2
(45) Date of Patent: May 16, 2023

(54) RICE CULTIVAR 'LYNX'

(71) Applicant: THE BOARD OF TRUSTEES OF THE UNIVERSITY OF ARKANSAS, Little Rock, AR (US)

(72) Inventor: Xueyan Sha, Stuttgart, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 184 days.

(21) Appl. No.: 17/077,210

(22) Filed: Oct. 22, 2020

(65) Prior Publication Data

US 2022/0125000 A1 Apr. 28, 2022

(51) Int. Cl.
*A01H 5/10* (2018.01)
*A01H 6/46* (2018.01)

(52) U.S. Cl.
CPC .......... *A01H 6/4636* (2018.05); *A01H 5/10* (2013.01)

(58) Field of Classification Search
None
See application file for complete search history.

(56) References Cited

U.S. PATENT DOCUMENTS

| | | |
|---|---|---|
| 6,281,416 B1 | 8/2001 | Moldenhauer |
| 7,429,697 B2 | 9/2008 | Moldenhauer |
| 9,693,520 B1 * | 7/2017 | Andaya ............... A01H 5/10 |

OTHER PUBLICATIONS

Bollich, C.N. et al. 1990. Registration of 'Rico 1' rice. Crop Science 30:1161.
Horsch, R.B., et al. "A simple and general method for hybridization revealed the expected." Science 227 (1985): 1229-1231.
Linscombe, S.D., et al. 1993. Registration of 'Bengal' rice. Crop Science 33:645-646.
Linscombe, S.D., et al. 2001. Registration of 'Earl' rice. Crop Science 41:2003-2004.
McKenzie, K.S., et al. 1988. Registration of 'Mercury' rice. Crop Science 28:193-194.
Sha, X., et al. 2006 Registration of 'Jupiter' rice. Crop Science 46:1811-1812.

* cited by examiner

*Primary Examiner* — Medina A Ibrahim
(74) *Attorney, Agent, or Firm* — Quarles & Brady, LLP

(57) ABSTRACT

A rice cultivar designated 'Lynx' is disclosed herein. The present invention provides seeds, plants, and plant parts derived from rice cultivar Lynx. Further, it provides methods for producing a rice plant by crossing Lynx with itself or another rice variety. The invention also encompasses any rice seeds, plants, and plant parts produced by the methods disclosed herein, including those in which additional traits have been transferred into Lynx through the introduction of a transgene or by breeding Lynx with another rice cultivar.

18 Claims, No Drawings

RICE CULTIVAR 'LYNX'

BACKGROUND OF THE INVENTION

The present invention relates to a new and distinctive rice cultivar, designated 'Lynx.'

Rice is an ancient agricultural crop and is today one of the principal food crops of the world. There are two cultivated species of rice: *Oryza sativa* L., the Asian rice, and *O. glaberrima* Steud., the African rice. *O. sativa* L. constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are preferred rice-producing soils because they minimize water losses from soil percolation. Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached sufficient size (four- to five-leaf stage), a shallow permanent flood of water, 5 to 16 cm deep, is applied to the field for the remainder of the crop season.

In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems predominant in their respective region. Thus, a drill-seeded breeding nursery is used by breeders in a region where rice is drill-seeded and a water-seeded nursery is used in regions where water-seeding is prominent.

Rice in the United States is classified into three primary market types by grain size, shape, and chemical composition of the endosperm: long-grain, medium-grain and short-grain. Typical U.S. long-grain cultivars cook dry and fluffy when steamed or boiled, whereas medium and short-grain cultivars cook moist and sticky. Traditionally, in the southern states, long-grain cultivars have been grown and generally receive higher market prices.

Rice, *Oryza sativa* L., is an important and valuable field crop. A continuing goal of plant breeders is to produce stable, high yielding rice cultivars that are agronomically sound. To accomplish this goal, rice plants with traits that result in superior cultivars must be developed.

SUMMARY OF THE INVENTION

The present invention provides a novel rice cultivar designated Lynx. The invention encompasses the seeds, plants, and plant parts of rice cultivar Lynx, as well as plants with essentially all of the physiological and morphological characteristics of Lynx.

This invention also provides methods for producing a rice plant by planting a plurality of seeds or by crossing rice Lynx with itself or another rice line. Any plant breeding methods using rice cultivar Lynx are part of this invention, including selfing, backcrosses, hybrid production, and crosses to populations. All plants and seeds produced using rice cultivar Lynx as a parent are within the scope of this invention, including gene-converted plants of Lynx. Methods for introducing a gene into Lynx, either through traditional breeding or transformation, are provided herein.

In still another aspect, the present invention provides regenerable cells for use in tissue culture of rice plant Lynx, as well as rice plants regenerated from these tissue cultures.

Definitions

To provide a clear and consistent understanding of the specification and claims, the following definitions are provided:

Apparent starch amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation ($F_1$) hybrid may be crossed with one of the parental lines used to produce the $F_1$ hybrids.

Breeding. The genetic manipulation of living organisms.

Cell. As used herein, this term includes isolated cells, cells grown in tissue culture, and cells that comprise a plant or plant part.

Cultivar. Used interchangeably with "variety". Refers to plants that are defined by the expression of the characteristics resulting from a given genotype or combination of genotypes, distinguished from any other plant grouping by the expression of at least one characteristic.

Days to 50% heading. The average number of days from emergence to the day when 50% of all panicles are exerted at least partially through the leaf sheath. A measure of maturity.

Embryo. The plant embryo is the part of a seed or bud that contains the earliest forms of the new plant's roots, stem and leaves.

Essentially all of the physiological and morphological characteristics. A plant having "essentially all the physiological and morphological characteristics" of the cultivar exhibits the characteristics of the cultivar with the exception of any characteristics derived from a converted gene.

F#. Denotes a filial generation, wherein the # is the generation number. For example, F1 is the first filial generation.

Gene. Refers to a unit of inheritance corresponding to a distinct sequence of DNA or RNA nucleotides that form part of a chromosome. A gene may encode a polypeptide or a nucleic acid molecule that has a function in the cell or organism.

Gene-converted. Describes a plant wherein essentially all of the desired morphological and physiological characteristics of a parental variety are maintained with the exception of a single trait that was transferred into the variety via backcrossing or genetic engineering.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Head rice. Kernels of milled rice in which greater than ¾ of the kernel is unbroken.

Herbicide resistant. Describes a plant that is tolerant or resistant to an herbicide at a level that would normally kill or inhibit the growth of a normal or wild-type rice plant.

Hybrid. Refers to the offspring or progeny of genetically dissimilar plant parents or stock produced as the result of controlled cross-pollination as opposed to a non-hybrid seed produced as the result of natural pollination.

Kernal length (L). Length of a rice grain, measured in millimeters.

Kernal width (W). Width of a rice grain, measured in millimeters.

Length/width (L/W) ratio. Determined by dividing the average length (L) by the average width (W).

Lodging. The percentage of plant stems that are leaning or have fallen to the ground before harvest. Lodging is determined by visual scoring, in which crops are rated from 0% (all plants standing) to 100% (all plant in plot lying flat on the soil surface). Lodged plants are difficult to harvest and reduce yield and grain quality. Lodging resistance is also called "straw strength".

Milling yield. The total amount of milled rice (whole and broken kernels) recovered after milling (i.e., removal of hulls, bran, and germ). In contrast, head rice yield is the total amount of whole kernels recovered after milling. Both values are expressed as a weight percentage of the original paddy or rough rice sample that was milled. For example, for a sample of 100 grams of rough rice, a milling yield of 65/70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and parts of plants, such as embryos, pollen, ovules, flowers, glumes, panicles, leaves, stems, roots, root tips, anthers, and pistils.

Plant height. Measured in centimeters from the soil surface to the tip of the extended panicle at harvest.

Plant parts. Includes, without limitation, protoplasts, leaves, stems, roots, root tips, anthers, pistils, seed, grain, embryo, pollen, ovules, cotyledon, hypocotyl, pod, flower, shoot, tissue, petiole, cells, and meristematic cells.

Progeny. Includes an $F_1$ rice plant produced from the cross of two rice plants, as well as plants produced from subsequent generational crosses (e.g., $F_2$, $F_3$, $F_4$, $F_5$, $F_6$, $F_7$, $F_8$, $F_9$, and $F_{10}$) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots and the like. However, in preferred embodiments, it refers to true seeds.

Trait. Refers to an observable and/or measurable characteristic of an organism. For example, the present invention describes plants that have a trait that make them resistant to fluazifop herbicides.

Transgenic. Describes an organism or cell that contains genetic material that has been artificially introduced.

Wild-type. When made in reference to a gene, "wild-type" refers to a functional gene common throughout a plant population and, thus, arbitrarily designated the "normal" or "wild-type" form of the gene.

DETAILED DESCRIPTION OF THE INVENTION

The present invention provides a novel rice cultivar designated Lynx. The invention encompasses both the seeds of this cultivar and plants grown from these seeds. The invention further encompasses any rice plant having essentially all of the physiological and morphological characteristics rice cultivar Lynx.

As used herein, the term plant includes plant cells, plant protoplasts, plant cell tissue cultures from which rice plants can be regenerated, plant calli, plant clumps and plant cells that are intact in plants or parts of plants, such as embryos, pollen, ovules, flowers, glumes, panicles, leaves, stems, roots, root tips, anthers, pistils, and the like.

Development and Characterization of Rice Cultivar Lynx

Rice cultivar Lynx (Poaceae Oryzea *Oryza sativa* L.) is a high yielding, early maturing, and short stature medium-grain rice experimental line. It was originally selected from the cross number 13CRS202 with a pedigree of 'Earl'/RU9902028//'Jupiter' made in Stuttgart, Ark. in spring 2013. RU9902028 is an unreleased medium-grain line developed near Crowley, La. with the pedigree of 'Bengal'//'Mercury'/'Rico 1'. Earl, Bengal, Mercury, and Jupiter are southern medium-grain rice cultivars (Linscombe, et al., 2001, Linscombe et al., 1993, McKenzie et al., 1988, and Sha et al., 2006), while Rico 1 is a high yielding, midseason, conventional height medium grain cultivar that was released in 1987 (Bollich et al., 1990). Lynx initiated as a $F_4$ bulk of a single progeny row 14X3334 at the Puerto Rico winter nursery near Lajas, Puerto Rico in spring 2014. It was bred using hybridization, a combination of modified pedigree and bulk breeding methods, and is adapted to the Southern U.S. rice growing region. It was evaluated in the preliminary Stuttgart initial trial (SIT) in 2015 as entry 15SIT898, and advanced to the Arkansas Rice Performance Trial (ARPT) and the Cooperative Uniform Regional Rice Nurseries (URRN) in 2016 and 2017, respectively, with the experimental designation RU1701121 (RU number indicates URRN; 17 indicates that the year entered was 2017; 01 indicates Stuttgart, Ark.; and 121 its entry number). The cultivar designation of 'Lynx' and the experimental designation of RU1701121 are used interchangeably herein. Lynx was also tested in the Advanced/Elite Line Yield Trial (AYT) in 2016 and 2018-2019, the Producer Rice Evaluation Program (PREP) and the Medium-Grain Producer Rice Evaluation Program (PREP-MG) trials in 2019, and the DD50 Rice Management Program at Stuttgart and Pine Tree in 2019, as well as in the Louisiana State University Agricultural Center's Rice Research Station (LSU-RRS) Commercial Advanced (CA) Yield Trial in 2019.

Lynx has shown an outstanding yield potential, good milling and grain quality, and good lodging and blast resistance compared with 'Jupiter' and 'Titan' in 62 statewide and regional replicated trials during 2016-2019. The average grain yield at 120 g kg$^{-1}$ moisture of Lynx is 9,336 pounds/acre or 207 bushels/acre compared with 9,077 or 202 of Jupiter, and 9,066 or 201 of Titan, respectively. Average milling yields (g kg$^{-1}$ whole milled kernels: g kg$^{-1}$ total milled rice) at 30 state and regional tests from 2016-2019 were 586:684 for Lynx, 607:683 for Jupiter, and 582:692 for Titan. Lynx averaged 102 cm in height in yield trials across Mid-South that is slightly taller than the 97 and 99 cm of Jupiter and Titan, respectively. Lynx has a similar maturity to Jupiter but is much later than Titan. The average number of days from emergence to 50% heading is 86 as compared to 86 and 81 for Jupiter and Titan, respectively.

Lynx has a plump, medium grain size like that of Titan, which is significantly larger than that of Jupiter. Analyses on 14 different sets of ARPT samples collected across Arkansas during 2016-2018 showed that the average length and width (mm), length/width ratio, and kernel weight (mg) of milled whole kernels of Lynx are 6.00, 2.64, 2.27, and 23.35, as compared to 5.75, 2.60, 2.22, and 21.46 for Jupiter, and 6.01, 2.58, 2.34, and 22.64 for Titan, respectively. Lynx has an average chalkiness value of 2.16% as compared to the 2.09 of Jupiter and 1.80 of Titan, respectively. Average apparent amylose content of Lynx is 156 g kg$^{-1}$ compared with the 164 and 161 g kg$^{-1}$ of Jupiter and Titan, respectively. Lynx has a low gelatinization temperature of 62.7° C., which is similar to the 62.1° C. and 62.9° C. of Jupiter and Titan, respectively. These results indicate that Lynx has the typical U.S. medium-grain rice cooking characteristics.

In inoculated tests, Lynx showed moderate susceptibility to leaf blast (*Pyricularia grisea* (Cooke) Sacc.) with a rating of 4.9 on a disease scale of 0=immune, 9=highly susceptible, as compared with the 5.0 and 4.8 of Jupiter and Titan, respectively. Molecular marker data indicated that Lynx, like Titan, possesses the blast resistant genes Pi-z and Pi-ks, while Jupiter possesses only the Pi-ks gene. In greenhouse inoculated tests, Lynx was rated susceptible to blast races IB-1, IB-17, and IB-49, but resistant to IC-17, and moderately resistant to IE-1, IE1-K, IG-1, and Under natural infestation or inoculated tests, Lynx appeared susceptible to sheath blight (*Rhizoctonia solani* Kühn), bacterial panicle blight (*Burkholderia glumae*), kernel smut (*Neovossia horrida*), and false smut (*Ustilaginoidea virens* (Cooke) Takah).

The leaves, lemma, and palea of Lynx are glabrous. The spikelet is straw colored. The apiculus is white at heading and becomes straw-colored as grains approach maturity. The grain is non-aromatic.

The variants observed and removed from increase fields of Lynx were primarily shorter and earlier. Other variants included any combination of the following: pubescent; later; taller; short-, intermediate-, and long-grain types; and golden and black hull. Other atypical plants may still be encountered in the variety. The total number of variants numbered less than 1 per 5000 plants.

The above-mentioned characteristics of rice cultivar Lynx are based primarily on data collected in Stuttgart, Ark. and are summarized in Table 1. The results of the various rice performance trials and additional data (e.g., agronomical characteristics, and disease reactions) are provided in Tables 2-28.

TABLE 1

Distinguishing Characteristics of Morphology and Physiology

Plant:

Grain type: Medium
Days to maturity (Seeding to 50% heading): 86
Plant height: 107 cm (range 99-109 cm)
Plant color (at booting): Green
Culm:

Angle (degrees from perpendicular after flowering): Erect (less than 30°)
Flag leaf (after heading):

Pubescence: Glabrous
Leaf angle (after heading): Intermediate
Blade color (at heading): Green
Panicle:

Length: 20.4 cm
Type: Compact
Exsertion (near maturity): Well

TABLE 1-continued

Distinguishing Characteristics of Morphology and Physiology

Axis: Droopy
Shattering (at maturity): Low (1-5%)
Grain (spikelet):

Awns (after full heading): Absent
Apiculus color: White
Stigma color: White and yellow
Lemma and palea color (at maturity): Straw
Lemma and palea pubescence: Glabrous
Grain (seed):

Seed coat color: Light brown
Scent: Nonscented
Shape class (length/width ratio):

Paddy: Medium (2.3:1 to 3.3:1)
Brown: Medium (2.1:1 to 3.0:1)
Milled: Medium (2.0:1 to 2.9:1)
Size: 27.2 g/1000 seeds milled rice
Disease resistance:

Rice blast (*Pyricularia grisea* (Cooke) Sacc.): Moderately susceptible
Sheath blight (*Rhizoctonia solani* Kuhn): Moderately susceptible
False smut (*Ustilaginoidea virens* (Cooke) Takah.): Susceptible
Bacterial panicle blight (*Burkholderia glumae* and *B. gladioli*): Susceptible
Narrow brown leaf spot (*Sphaerulina oryzina*): Moderately resistant

TABLE 2

Overall average grain yield (at 12% H$_2$O) and milling yields (% head and total rice) of Lynx (Experimental name: RU1701121 in the table) and check varieties, 2016-2019.

| Variety | Gram Yield (Bu/A) | Grain Yield (Lb/A) | Milling Yield (%) Head Rice | Milling Yield (%) Total Rice |
|---|---|---|---|---|
| RU1701121 | 207 | 9,336 | 58.6 | 68.4 |
| Jupiter | 202 | 9,077 | 60.7 | 68.3 |
| Titan | 201 | 9,066 | 58.2 | 69.2 |
| No. trials | 62 | 62 | 31 | 31 |

TABLE 3

Overall average days to 50% heading, plant height, and lodging incidence of Lynx (Experimental name: RU1701121 in the table) and check varieties, 2016-2019.

| Variety | Seedling vigor† | Days to 50% heading | Plant height (inch) | Lodging incidence (%) |
|---|---|---|---|---|
| RU1701121 | 3.9 | 86 | 40 | 3.6 |
| Jupiter | 3.7 | 86 | 38 | 2.1 |
| Titan | 3.1 | 81 | 39 | 1.0 |
| No. trials | 19 | 45 | 43 | 62 |

†Subjective rating 1-7, 1 = perfect stand and 7 = no stand.

TABLE 4

Milling yields (by McGill No. 2 test mill) and average amylose content, gelatinization temperature, chalkiness of Lynx and check varieties analyzed by Riceland Foods, Inc. Stuttgart, Arkansas on Arkansas Rice Performance Trial (ARPT) samples collected across the state, 2016-2018. (Lynx experimental name: RU1701121 in the table)

| Variety | Milling yield (%) Head rice | Milling yield (%) Total rice | Amylose content (%) | Gel temperature (° C.) | Chalkiness (%) |
|---|---|---|---|---|---|
| RU1701121 | 66.1 | 70.4 | 15.6 | 62.7 | 2.2 |
| Jupiter | 67.7 | 70.2 | 16.4 | 62.2 | 2.1 |
| Titan | 65.3 | 70.9 | 16.1 | 62.9 | 1.8 |
| No. trials | 14 | 14 | 14 | 14 | 14 |

TABLE 5

Kernel dimension and weight of milled rice of Lynx (Experimental name: RU1701121 in the table) and check varieties analyzed by Riceland Foods, Inc., Stuttgart, Arkansas on Arkansas Rice Performance Trial (ARPT) samples collected across the state, 2016-2018.

| Variety | Length (L) mm | Width (W) mm | Thickness mm | L/W ratio | Kernel weight (mg) |
|---|---|---|---|---|---|
| RU1701121 | 6.00 | 2.64 | 1.88 | 2.27 | 23.35 |
| Jupiter | 5.75 | 2.60 | 1.85 | 2.22 | 21.46 |
| Titan | 6.01 | 2.58 | 1.84 | 2.34 | 22.64 |
| No. trials | 14 | 14 | 14 | 14 | 14 |

TABLE 6

Rapid viscosity analysis (RVA) results of Lynx (Experimental name: RU1701121 in the table) and check varieties analyzed by Riceland Foods, Inc., Stuttgart, Arkansas on Arkansas Rice Performance Trial (ARPT) samples collected across the state, 2016-2018.

| Variety | Peak Viscosity | Trough | Breakdown | Final Viscosity | Setback |
|---|---|---|---|---|---|
| RU1701121 | 286 | 149 | 137 | 248 | −39 |
| Jupiter | 277 | 147 | 130 | 246 | −31 |
| Titan | 288 | 140 | 147 | 236 | −51 |
| No. trials | 14 | 14 | 14 | 14 | 14 |

TABLE 7

Average disease rating (on a 0-9, 0 = immune and 9 = maximum) of Lynx (Experimental name: RU1701121 in the table) and check varieties against sheath blight, leaf blast, rotten neck blast, and bacterial panicle blight under inoculation, 2016-2019. (Dr. Don Groth, 2017-2019, personal communications).

| Variety | Sheath blight | Leaf blast | Rotten neck blast | Bacterial panicle blight |
|---|---|---|---|---|
| RU1701121 | 5.2 | 4.9 | 2.2 | 3.9 |
| Jupiter | 5.4 | 5.0 | 1.0 | 2.5 |
| Titan | 6.3 | 4.8 | 2.6 | 4.1 |
| No. trials | 3 | 3 | 3 | 3 |

TABLE 8

Disease reactions (on a 0-9 rating scale, 0 = immune and 9 = maximum) of Lynx and check varieties inoculated with different races of blast pathogen (Pyricularia oryzae) in the greenhouse, Stuttgart, AR. 2016. (Scott Belmar, personal communication, 2016-2017, 2019).

| Variety | IB-1 | IB-17 | IB-49 | IC-17 | IE-1 | IE1-K | IG-1 | IH-1 |
|---|---|---|---|---|---|---|---|---|
| Lynx | S† | S | S | R | MR | MR | MR | MR |
| Jupiter | S | S | S | R | MS | S | S | S |
| Titan | S | S | S | R | MR | MR | MR | MR |
| No. trials | 3 | 2 | 3 | 3 | 1 | 3 | 1 | 1 |

†Disease reaction, R = resistant, MR = moderately resistant, MS = moderately susceptible, and S = susceptible.

TABLE 9

Lynx Reactions to diseases and lodging. (Yeshi Wamishe, personal communication, 2019) (Lynx experimental name: RU1701121 in the table).

| Variety | Sheath Blight | Blast | Straight-head | Bacterial Panicle Blight | Narrow Brown Leaf Spot | Stem Rot | Kernel Smut | False Smut | Lodging | Black Sheath Rot | Sheath Spot |
|---|---|---|---|---|---|---|---|---|---|---|---|
| RU1701121 | S | MS | — | S | MR | — | — | MS | — | — | — |

Reaction: R = Resistant; MR = Moderately Resistant; MS = Moderately Susceptible; S = Susceptible; VS = Very Susceptible (cells with no values indicate no definitive Arkansas disease rating information is available at this time). Reactions were determined based on recent observations from test plots across Arkansas. In general, these ratings represent expected cultivar reactions to disease under conditions that most favor severe disease development.

TABLE 10

Average grain yield of Lynx (Experimental name: RU1701121 in the table) and check varieties by location in the Arkansas Rice Performance Trial (ARPT) across rice growing regions of Arkansas, 2016-2019. (Dr. Jarrod Hardke, personal communication, 2019).

| | Grain yield (bushels/acre at 12% H$_2$O) | | | | | | |
|---|---|---|---|---|---|---|---|
| Variety | Chicot† | Clay | NEC | NEREC | PTRS | RREC | Mean |
| RU1701121 | 207 | 202 | 125 | 208 | 196 | 213 | 201 |
| Jupiter | 201 | 195 | 132 | 209 | 179 | 215 | 196 |
| Titan | 192 | 215 | 155 | 199 | 181 | 218 | 201 |

†Test location: Chicot = Chicot Co., AR., Clay = Clay Co., AR., NEC = Newport Extension Center near Newport, AR., NEREC = Northeast Research and Extension Center at Keiser, AR., PTRS = Pine Tree Research Station near Colt, AR., and RREC = Rice Research and Extension Center near Stuttgart, AR. During 2016-2019, each year trials were conducted at all locations except for Chicot (2017-2018 only) and NEC (2016 only).

TABLE 11

Average milling yields of Lynx (Experimental name: RU1701121 in the table) and check varieties in the Arkansas Rice Performance Trial (ARPT) conducted at six Arkansas locations, 2016-2018. (Dr. Jarrod Hardke, personal communication, 2019).

| | Milling yields (% head rice-% total rice) | | | | | | |
|---|---|---|---|---|---|---|---|
| Variety | Chicot† | Clay | NEC | NEREC | PTRS | RREC | Mean |
| RU1701121 | 50-69 | 48-69 | 51-68 | 50-67 | 50-66 | 60-68 | 52-68 |
| Jupiter | 56-69 | 54-70 | 55-69 | 58-67 | 54-66 | 60-69 | 56-68 |
| Titan | 46-69 | 47-70 | 44-69 | 51-68 | 50-67 | 57-70 | 51-69 |

†Test location: Chicot = Chicot Co., AR., Clay = Clay Co., AR., NEC = Newport Extension Center near Newport, AR., NEREC = Northeast Research and Extension Center at Keiser, AR., PTRS = Pine Tree Research Station near Colt, AR., and RREC = Rice Research and Extension Center near Stuttgart, AR. During 2016-2019, each year trials were conducted at all locations except for Chicot (2017-2018 only) and NEC (2016 only).

TABLE 12

Overall agronomical characteristics of Lynx (Experimental name: RU1701121 in the table) and check varieties in the Arkansas Rice Performance Trial (ARPT) at six Arkansas locations, 2016-2019. (Dr. Jarrod Hardke, personal communication, 2019).

| Variety | Days to 50% heading | Height (inch) | Lodging (%) |
|---|---|---|---|
| RU1701121 | 87 | 38 | 5.4 |
| Jupiter | 87 | 36 | 4.5 |
| Titan | 81 | 38 | 1.8 |

TABLE 13

Grain yield of Lynx (Experimental name: RU1701121 in the table) and check varieties in 2019 Arkansas Rice Performance Trial (ARPT) at five Arkansas locations. (Dr. Jarrod Hardke, personal communication, 2019).

| | Grain yield (bushels/acre at 12% H$_2$O) | | | | |
|---|---|---|---|---|---|
| Variety | Clay† | NEREC | PTRS | RREC | Mean |
| RU1701121 | 209 | 229 | 185 | 237 | 215 |
| Jupiter | 200 | 230 | 198 | 246 | 218 |
| Titan | 235 | 222 | 190 | 228 | 219 |

†Test location: Clay = Clay Co., AR., NEREC = Keiser, AR., PTRS = Colt, AR., and RREC = Stuttgart, AR.

TABLE 14

Grain yield of Lynx (Experimental name: RU1701121 in the table) and check varieties in 2018 Arkansas Rice Performance Trial (ARPT) at five Arkansas locations. (Dr. Jarrod Hardke, personal communication, 2018).

| | Grain yield (bushels/acre at 12% H$_2$O) | | | | | |
|---|---|---|---|---|---|---|
| Variety | Chicot† | Clay | NEREC | PTRS | RREC | Mean |
| RU1701121 | 206 | 216 | 169 | 218 | 218 | 205 |
| Jupiter | 192 | 230 | 191 | 177 | 207 | 199 |
| Titan | 177 | 216 | 160 | 201 | 208 | 192 |

†Test location: Chicot = Chicot Co., AR., Clay = Clay Co., AR., NEREC = Keiser, AR., PTRS = Colt, AR., and RREC = Stuttgart, AR.

TABLE 15

Milling yields of Lynx (Experimental name: RU1701121 in the table) and check varieties in 2018 Arkansas Rice Performance Trial (ARPT) conducted at five Arkansas locations, 2018. (Dr. Jarrod Hardke, personal communication, 2018).

| | Milling yields (% head rice-% total rice) | | | | | |
|---|---|---|---|---|---|---|
| Variety | Chicot† | Clay | NEREC | PTRS | RREC | Mean |
| RU1701121 | 39-72 | 60-70 | 33-67 | 51-69 | 61-69 | 49-69 |
| Jupiter | 40-71 | 58-70 | 52-66 | 54-68 | 61-68 | 53-69 |
| Titan | 27-71 | 60-70 | 33-68 | 47-69 | 64-70 | 46-70 |

†Test location: Chicot = Chicot Co., AR., Clay = Clay Co., AR., NEREC = Northeast Research and Extension Center at Keiser, AR., PTRS = Pine Tree Research Station near Colt, AR., and RREC = Rice Research and Extension Center near Stuttgart, AR.

TABLE 16

Grain yield of Lynx (Experimental name: RU1701121 in the table) and check varieties in 2017 Arkansas Rice Performance Trial (ARPT) conducted at five Arkansas locations. (Dr. Jarrod Hardke, personal communication, 2017).

| | Grain yield (bushels/acre at 12% H$_2$O) | | | | | |
|---|---|---|---|---|---|---|
| Variety | Chicot† | Clay | NEREC | PTRS | RREC | Mean |
| RU1701121 | 208 | 222 | 208 | 191 | 201 | 206 |
| Jupiter | 208 | 218 | 210 | 184 | 198 | 203 |
| Titan | 212 | 198 | 214 | 164 | 214 | 200 |

†Test location: Chicot = Chicot Co., AR., Clay = Clay Co., AR., NEREC = Northeast Research and Extension Center at Keiser, AR., PTRS = Pine Tree Research Station near Colt, AR., and RREC = Rice Research and Extension Center near Stuttgart, AR.

TABLE 17

Milling yields of Lynx (Experimental name: RU1701121 in the table) and check varieties in 2017 Arkansas Rice Performance Trial (ARPT) conducted at five Arkansas locations. (Dr. Jarrod Hardke, personal communication, 2017).

| | Milling yields (% head rice-% total rice) | | | | | |
|---|---|---|---|---|---|---|
| Variety | Chicot† | Clay | NEREC | PTRS | RREC | Mean |
| RU1701121 | 40-68 | 60-70 | 59-67 | 45-65 | 62-67 | 53-67 |
| Jupiter | 54-68 | 61-70 | 64-68 | 55-65 | 62-65 | 59-67 |
| Titan | 33-68 | 49-69 | 60-69 | 50-66 | 61-67 | 51-68 |

†Test location: Chicot = Chicot Co., AR., Clay = Clay Co., AR., NEREC = Northeast Research and Extension Center at Keiser, AR., PTRS = Pine Tree Research Station near Colt, AR., and RREC = Rice Research and Extension Center near Stuttgart, AR.

TABLE 18

Grain yield of Lynx (Experimental name: RU1701121 in the table) and check varieties in 2016 Arkansas Rice Performance Trial (ARPT) conducted at five Arkansas locations. (Dr. Jarrod Hardke, personal communication, 2016).

| | Grain yield (bushels/acre at 12% $H_2O$) | | | | | |
|---|---|---|---|---|---|---|
| Variety | Clay† | NEC | NEREC | PTRS | RREC | Mean |
| RU1701121 | 158 | 125 | 210 | 192 | 195 | 176 |
| Jupiter | 133 | 132 | 207 | 157 | 207 | 167 |
| Titan | 209 | 155 | 201 | 170 | 223 | 192 |

†Test location: Clay = Clay Co., AR., NEC = Newport Extension Center near Newport, AR., NEREC = Northeast Research and Extension Center at Keiser, AR., PTRS = Pine Tree Research Station near Colt, AR., and RREC = Rice Research and Extension Center near Stuttgart, AR.

TABLE 19

Milling yields of Lynx (Experimental name: RU1701121 in the table) and check varieties in 2016 Arkansas Rice Performance Trial (ARPT) conducted at five Arkansas locations. (Dr. Jarrod Hardke, personal communication, 2016).

| | Milling yields (% head rice-% total rice) | | | | | |
|---|---|---|---|---|---|---|
| Variety | Clay† | NEC | NEREC | PTRS | RREC | Mean |
| RU1701121 | 47-68 | 51-68 | 56-67 | 52-63 | 60-66 | 53-66 |
| Jupiter | 58-70 | 55-69 | 59-70 | 52-65 | 59-69 | 56-69 |
| Titan | 55-69 | 44-69 | 59-70 | 53-66 | 58-70 | 54-69 |

†Test location: Clay = Clay Co., AR., NEC = Newport Extension Center near Newport, AR., NEREC = Northeast Research and Extension Center at Keiser, AR., PTRS = Pine Tree Research Station near Colt, AR., and RREC = Rice Research and Extension Center near Stuttgart, AR.

TABLE 20

Preliminary yield data of Lynx (Experimental name: RU1701121 in the table) and check varieties in 2019 Producer Rice Evaluation Program (PREP) trials conducted at six locations across rice growing area of Arkansas. (Dr. Jarrod Hardke, personal communication, 2019).

| | Grain yield (bushels/acre at 12% $H_2O$) | | | | | | |
|---|---|---|---|---|---|---|---|
| Variety | GRE† | LEE | LON | POI | PRA | WOO | Mean |
| RU1701121 | 189 | 244 | | 172 | 191 | 198 | 199 |
| Jupiter | 207 | 250 | | 222 | 206 | 217 | 220 |
| Titan | 184 | 219 | | 230 | 196 | 253 | 217 |

†Test location: GRE = Greene Co., LEE = Lee Co., LON = Lonoke Co., POI = Poinsett Co., PRA = Prairie Co., and WOO = Woodruff Co.

TABLE 21

Performance of Lynx (Experimental name: RU1701121 in the table) and check varieties in 2019 Medium-grain Producer Rice Evaluation Program (PREP-MG) trials conducted at Poinsett Co, Arkansas. (Dr. Jarrod Hardke, personal communication, 2019).

| Variety | Days to 50% heading | Height (in) | Yield (bu/A) | Head rice (%) | Total rice (%) |
|---|---|---|---|---|---|
| RU1701121 | 92 | 32 | 192 | | |
| Jupiter | 91 | 30 | 185 | | |
| Titan | 89 | 28 | 175 | | |

TABLE 22

Average grain yield of Lynx (Experimental name: RU1701121 in the table) and check varieties in 2019 DD50* trial, Stuttgart, AR. (Dr. Jarrod Hardke, personal communication, 2019).

| | Grain yield (bushels/acre at 12% $H_2O$) | | | | | | |
|---|---|---|---|---|---|---|---|
| Variety | Mar-21† | Apr-3 | Apr-16 | Apr-29 | May-17 | Jun-4 | Mean |
| RU1701121 | 253 | 243 | 225 | 231 | 213 | 203 | 228 |
| Jupiter | 248 | 229 | 238 | 227 | 210 | 198 | 225 |
| Titan | 239 | 226 | 230 | 217 | 208 | 207 | 221 |

†Planting date.
*The DD50 program was developed in the 1970's to help rice farmers accurately time mid-season nitrogen applications. The DD50 is a modification of the growing degree-day concept, which uses temperature data to predict rice development.

TABLE 23

Average grain yield of Lynx (Experimental name: RU1701121 in the table) and check varieties in 2019 DD50 trial, Pine Tree, AR. (Dr. Jarrod Hardke, personal communication, 2019).

| | Grain yield (bushels/acre at 12% $H_2O$) | | | | | |
|---|---|---|---|---|---|---|
| Variety | Apr-2† | Apr-24 | May-8 | May-28 | Jun-12 | Mean |
| RU1701121 | 199 | 245 | 227 | 185 | | 214 |
| Jupiter | 159 | 231 | 210 | 188 | | 197 |
| Titan | 137 | 232 | 189 | 183 | | 185 |

†Planting date.

TABLE 24

Performance of Lynx (Experimental name: RU1701121 in the table) and check varieties in the Louisiana Commercial Advanced (CA) trials and the Uniform Regional Rice Nursery (URRN) conducted at five location across Louisiana rice growing regions, 2017-2019. (Dr. Adam Famoso, personal communication, 2019).

| Variety | Days to 50% heading | Height (in) | Yield (bu/A) | Head rice (%) | Total rice (%) |
|---|---|---|---|---|---|
| RU1701121 | 85 | 39 | 203 | 62.8 | 68.1 |
| Jupiter | 85 | 38 | 191 | 60.0 | 67.3 |
| Titan | 81 | 39 | 202 | 63.6 | 69.1 |

TABLE 25

Average yield, milling, and agronomical characteristics of Lynx (Experimental name: RU1701121 in the table) and check varieties in the Uniform Regional Rice Nursery (URRN) tested in Stuttgart, AR, Crowley, LA, Stoneville, MS, Malden, MO, and Beaumont, TX, 2017-2019.

| Variety | Days to 50% heading | Height (cm) | Lodging (%) | Yield (bu/A) | Yield (lb/A) | Head rice (%) | Total rice (%) |
|---|---|---|---|---|---|---|---|
| 2017-2019 Average | | | | | | | |
| RU1701121 | 88 | 102 | 0 | 210 | 9,445 | 63.4 | 68.9 |
| Jupiter | 88 | 99 | 0 | 200 | 8,994 | 62.7 | 67.8 |
| Titan | 82 | 100 | 0 | 205 | 9,227 | 62.5 | 69.7 |
| 2017 | | | | | | | |
| RU1701121 | 89 | 100 | 0 | 208 | 9,346 | 63.5 | 69.6 |
| Jupiter | 90 | 94 | 0 | 197 | 8,869 | 61.7 | 67.9 |
| Titan | 84 | 101 | 0 | 221 | 9,931 | 62.6 | 70.0 |
| 2018 | | | | | | | |
| RU1701121 | 88 | 102 | 0 | 200 | 9,022 | 61.8 | 67.9 |
| Jupiter | 86 | 99 | 0 | 187 | 8,403 | 63.5 | 67.4 |
| Titan | 81 | 97 | 0 | 181 | 8,159 | 62.2 | 69.1 |

TABLE 25-continued

Average yield, milling, and agronomical characteristics of Lynx (Experimental name: RU1701121 in the table) and check varieties in the Uniform Regional Rice Nursery (URRN) tested in Stuttgart, AR, Crowley, LA, Stoneville, MS, Malden, MO, and Beaumont, TX, 2017-2019.

| Variety | Days to 50% heading | Height (cm) | Lodging (%) | Yield (bu/A) | Yield (lb/A) | Head rice (%) | Total rice (%) |
|---|---|---|---|---|---|---|---|
| 2019† | | | | | | | |
| RU1701121 | 86 | 105 | 0 | 238 | 10,701 | 66.8 | 71.1 |
| Jupiter | 83 | 99 | 0 | 219 | 9,866 | 64.3 | 68.3 |
| Titan | 79 | 96 | 0 | 233 | 10,490 | 66.0 | 70.9 |

†Only Arkansas and Louisiana data were available, and milling yields were from Louisiana.

TABLE 26

Performance of Lynx (Experimental name: RU1701121 in the table) and check varieties in 2018 Conventional Advanced Yield Trial, Stuttgart, AR.

| Variety | Seedling vigor† | Days to 50% heading | Height (in) | Yield (bu/A) |
|---|---|---|---|---|
| RU1701121 | 5.3 | 82 | 44 | 223 |
| Jupiter | 4.0 | 79 | 40 | 206 |
| Titan | 3.7 | 73 | 43 | 171 |

†Subjective rating 1-7, 1 = perfect stand and 7 = no stand.

TABLE 27

Performance of Lynx (Experimental name: RU1701121 in the table) and check varieties in the Advanced/Elite Line Yield Trial (AYT) conducted at Northeast Research and Extension Center (NEREC), Pine Tree Research Station (PTRS), and Rice Research and Extension Center (RREC), 2016, 2018-2019.

| Variety | Seedling vigor† | Days to 50% heading | Plant height (inch) | Lodging (%) | Yield (bu/A) | Head rice (%)‡ | Total rice (%)‡ |
|---|---|---|---|---|---|---|---|
| 3-Location Average | | | | | | | |
| RU1701121 | 3.3 | 85 | 38 | 0 | 213 | 65.8 | 68.6 |
| Jupiter | 3.1 | 85 | 37 | 0 | 200 | 67.0 | 68.9 |
| Titan | 3.1 | 80 | 37 | 0 | 199 | 66.7 | 69.3 |
| RREC | | | | | | | |
| RU1701121 | 3.6 | 85 | 41 | 0 | 203 | 64.6 | 67.6 |
| Jupiter | 3.1 | 85 | 37 | 0 | 190 | 66.8 | 69.2 |
| Titan | 3.3 | 81 | 39 | 0 | 196 | 67.0 | 69.1 |
| PTRS | | | | | | | |
| RU1701121 | 3.4 | 84 | 37 | 0 | 216 | 66.7 | 69.0 |
| Jupiter | 3.3 | 85 | 35 | 0 | 200 | 67.1 | 68.8 |
| Titan | 3.0 | 78 | 36 | 0 | 202 | 68.4 | 70.0 |
| NEREC | | | | | | | |
| RU1701121 | 3.0 | 86 | 37 | 0 | 220 | 66.0 | 69.1 |
| Jupiter | 3.0 | 86 | 37 | 0 | 212 | 66.9 | 68.6 |
| Titan | 3.0 | 79 | 37 | 0 | 198 | 64.8 | 69.0 |

†Subjective rating 1-7, 1 = perfect stand and 7 = no stand.
‡Test milling was conducted by Riceland Foods, Inc, Stuttgart, AR on the McGill No. 2 test mill.

TABLE 28

Grain yield of Lynx under different nitrogen (N) fertilizer rates in 2019 at Northeast Research and Extension Center (NEREC), Pine Tree Research Station (PTRS), and Rice Research and Extension Center (RREC), (Dr. Jarrod Hardke, personal communication, 2019).

| N Fertilizer Rate | Grain Yield | | |
|---|---|---|---|
| (lbs N/A) | NEREC | PTRS | RREC |
| | (bushels/acre) | | |
| 0 | 81 | 105 | 116 |
| 60 | | 162 | 172 |
| 90 | 158 | 187 | 197 |
| 120 | 171 | 203 | 205 |
| 150 | 195 | 219 | 222 |
| 180 | 214 | 229 | 218 |
| 210 | 221 | | |

Methods

This present invention provides methods for producing rice plants. In some embodiments, these methods involve crossing a first parent rice plant with a second parent rice plant wherein either the first or second parent rice plant is a rice plant of the line Lynx. Further, both first and second parent rice plants can come from the rice cultivar Lynx. Still further, this invention also is directed to methods for producing a rice cultivar Lynx-derived rice plant by crossing rice cultivar Lynx with a second rice plant and growing the progeny seed, and repeating the crossing and growing steps with the rice cultivar Lynx-derived plant from 0 to 7 times. Thus, any such methods using the rice cultivar Lynx are part of this invention: selfing, backcrosses, hybrid production, crosses to populations, and the like. All plants produced using rice cultivar Lynx as a parent are within the scope of this invention, including plants derived from rice cultivar Lynx. Advantageously, the rice cultivar is used in crosses with other, different, rice cultivars to produce first generation ($F_1$) rice seeds and plants with superior characteristics.

In some embodiments, a Lynx progeny plant is selected that has molecular markers, morphological characteristics, and/or physiological characteristics in common with Lynx (e.g., those listed in Table 1). Techniques such as RFLP-enhanced selection, genetic marker enhanced selection (e.g., SSR markers), and the making of double haploids may be utilized to identify progeny that share particular traits with Lynx.

Further, this invention provides methods for introducing a desired trait into rice cultivar Lynx. This may be accomplished using traditional breeding methods, such as back-crossing (see Breeding Methods section below). Alternatively, the desired trait may be introduced by transforming the rice cultivar with a transgene (see Transformation Methods section below). The transgenic cultivar produced by these methods may be crossed with another cultivar to produce a new transgenic cultivar. Alternatively, the trans-gene incorporated by these methods could be moved into another cultivar using traditional backcrossing techniques.

Optionally, any of the disclosed methods may further comprise additional steps involving producing rice seed from the resulting rice plants and/or planting the rice seed.

The present invention encompasses all plants, or parts thereof, produced by the methods described herein, as well as the seeds produced by these plants. Further, any plants derived from rice cultivar Lynx or produced from a cross using cultivar Lynx are provided. This includes genetic variants, created either through traditional breeding methods or through transformation, as well as plants produced in a male-sterile form. Notably, this includes gene-converted plants developed by backcrossing. Any of the seeds, plants, or plant parts provided may be utilized for human food, livestock feed, and as a raw material in industry.

The present invention also encompasses progeny of rice cultivar Lynx comprising a combination of at least two Lynx traits selected from those listed in the Tables and Detailed Description of the Invention, wherein the progeny rice plant is not significantly different from Lynx for said traits, as determined at the 5% significance level when grown in the same environment. One of skill in the art knows how to compare a trait between two plant varieties to determine if there is a significant difference between them (Fehr and Walt, Principles of Cultivar Development, pp. 261-286 (1987)). Molecular markers or mean trait values may be used to identify a plant as progeny of Lynx. Alternatively, progeny may be identified through their filial relationship with rice cultivar Lynx (e.g., as being within a certain number of breeding crosses of rice cultivar Lynx). For example, progeny produced by the methods described herein may be within 1, 2, 3, 4, or 5 breeding crosses of rice cultivar Lynx.

Tissue Culture

The present invention provides tissue cultures of regenerable cells or protoplasts produced from rice cultivar Lynx. As is well known in the art, tissue culture of rice can be used for the in vitro regeneration of a rice plant. Thus, such cells and protoplasts may be used to produce plants having the physiological and morphological characteristics of rice variety Lynx. The rice plants regenerated by these methods are also encompassed by the present invention.

As used herein, the term "tissue culture" describes a composition comprising isolated cells or a collection of such cells organized into parts of a plant. Exemplary tissues for culture include protoplasts, calli, plant clumps, and plant cells that can be grown in culture, or parts of plants, such as embryos, pollen, flowers, seeds, pods, leaves, stems, roots, root tips, and anthers. Culture of various rice tissues and regeneration of plants therefrom is well known in the art.

Breeding Methods

The goal of rice breeding is to develop new, superior rice cultivars and hybrids. A superior cultivar is produced when a new combination of desirable traits is formed within a single plant variety. Desirable traits may include higher seed yield, resistance to diseases and insects, better stems and roots, tolerance to low or high temperatures, herbicide resistance, and better agronomic characteristics or grain quality.

The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation.

Use of rice cultivar Lynx in any plant breeding method is encompassed by the present invention. The choice of a breeding or selection method will depend on several factors, including the mode of plant reproduction, the heritability of the trait(s) being improved, and the type of cultivar used commercially (e.g., F1 hybrid cultivar, pureline cultivar). Popular selection methods include pedigree selection, modified pedigree selection, mass selection, recurrent selection, backcrossing, or a combination thereof.

Pedigree selection is commonly used for the improvement of self-pollinating crops. Two parents are crossed to produce an $F_1$ population. An $F_2$ population is produced by selfing one or several $F_1$'s. Selection of the best individuals may begin in the $F_2$ population; then, beginning in the $F_3$ generation, the best individuals in the best families are selected. Replicative testing of families can begin in the $F_4$ generation to make selection of traits with low heritability more effective. At an advanced stage of inbreeding (e.g., $F_6$ or $F_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods

As is noted above, the present invention provides plants and seeds of rice cultivar Lynx in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. For example, the transgene may confer resistance to an herbicide selected from the group consisting of: glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. The vector may be a plasmid, and can be used alone or in combination with other plasmids.

Expression vectors include at least one genetic marker operably linked to a regulatory element (e.g., a promoter) that allows transformed cells containing the vector to be recovered by selection. In some embodiments, negative selection (i.e., inhibiting growth of cells that do not contain the selectable marker gene) it utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and Green Fluorescent Protein (GFP).

Transgene expression is typically driven by operably linking the transgene to a promoter within the expression vector. However, other regulatory elements may also be used to drive expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be "tissue-specific", "cell type-specific", "inducible", or "constitutive". Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in *Corn & Corn Improvement,* 3rd Edition; Sprague, et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch et al., *Science,* 227:1229 (1985). Descriptions of *Agrobacterium* vector systems and methods for *Agrobacterium*-mediated gene transfer are provided by Gruber, et al., supra.

REFERENCES

Bollich, C. N. Webb, B. D. and Marchetti, M. A., and Scott, J. E. 1990. Registration of 'Rico 1' rice. Crop Science 30:1161.

Linscombe, S. D., Jodari, F., Bollich, P. K., Groth, D. E., White, L. M., Chu, Q. R., Dunand R. T. and Sanders, D. E. 2001. Registration of 'Earl' rice. Crop Science 41:2003-2004.

Linscombe, S. D., Jodari, F., McKenzie, K. S., Bollich, P. K., Groth, D. E., White, L. M., Dunand, R. T., Sanders, D. E. 1993. Registration of 'Bengal' rice. Crop Science 33:645-646.

McKenzie, K. S., Bollich, P. K., Groth, D. E., Jodari, F., Robinson, J. F. and Rutger, J. N. 1988. Registration of 'Mercury' rice. Crop Science 28:193-194.

Sha, X., Linscombe, S. D., Chu, Q., Groth, D. E., White, L. M., Bond, J., Dunand, R. T., and Utomo, H. 2006 Registration of 'Jupiter' rice. Crop Science 46:1811-1812.

Deposit Information

A deposit of the University of Arkansas Division of Agriculture Rice Research and Extension Center proprietary rice cultivar Lynx disclosed above and recited in the appended claims has been made with the American Type Culture Collection (ATCC), 10801 University Boulevard, Manassas, Va. 20110. The date of deposit was Jan. 4, 2021. The deposit of 2,500 seeds was taken from the same deposit maintained by the University of Arkansas Division of Agriculture Rice Research and Extension Center (2900 Hwy 130 E., Stuttgart, Ark. 72160) since prior to the filing date of this application. All restrictions will be irrevocably removed upon granting of a patent, and the deposit is intended to meet all of the requirements of 37 C.F.R. §§ 1.801-1.809. The ATCC Accession Number is PTA-126945. The deposit will be maintained in the depository for a period of thirty years, or five years after the last request, or for the enforceable life of the patent, whichever is longer, and will be replaced as necessary during that period.

What is claimed is:

1. A rice seed of the cultivar 'Lynx,' a representative sample of seed of said cultivar having been deposited under ATCC Accession No. PTA-126945.

2. A rice plant, or a part thereof, produced by growing the seed of claim 1.

3. A rice plant, or a part thereof, having all of the physiological and morphological characteristics of the rice plant of claim 2.

4. Pollen or an ovule of the plant of claim 2.

5. A method for producing rice plants, said method comprising planting a plurality of rice seeds as recited in claim 1 under conditions favorable for the growth of rice plants.

6. The method of claim 5, further comprising the step of producing rice seed from the resulting rice plants.

7. A rice seed produced by the method of claim 6.

8. A tissue culture of regenerable cells or protoplasts produced from the rice plant of claim 2.

9. The tissue culture of claim 8, wherein said cells or protoplasts are produced from a tissue selected from the group consisting of embryos, meristematic cells, pollen, leaves, anthers, roots, root tips, pistils, anthers, cotyledon, hypocotyl, panicles, flowers, seeds, and stems.

10. A rice plant regenerated from the tissue culture of claim 8, said rice plant having all of the morphological and physiological characteristics of 'Lynx'.

11. A method for producing an $F_1$ hybrid rice plant, said method comprising crossing a first parent rice plant with a second parent rice plant, wherein the first parent rice plant or the second patent rice plant is the rice plant of claim 2.

12. The method of claim 11, further comprising the step of producing rice seed from the resulting rice plant.

13. The method of claim 11, wherein the second parent rice plant is transgenic.

14. A method comprising transforming the rice plant of claim 2 or cell thereof with a transgene, wherein the transgene confers at least one trait selected from the group consisting of: herbicide resistance; insect resistance; resistance to bacterial, fungal, or viral disease; modified fatty acid metabolism; modified carbohydrate metabolism; and male sterility.

15. A rice plant or cell thereof produced by the method of claim 14.

16. An herbicide resistant rice plant produced by the method of claim 14, wherein the gene confers resistance to a herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors and benzonitrile.

17. A method of introducing a desired trait into rice cultivar 'Lynx,' said method comprising the steps of:
   (a) crossing plants as recited in claim 2 with plants of another rice line expressing the desired trait, to produce progeny plants;
   (b) selecting progeny plants that express the desired trait, to produce selected progeny plants;
   (c) crossing the selected progeny plants with plants from the 'Lynx' parental line to produce new progeny plants;
   (d) selecting new progeny plants that express the desired trait; and
   (e) repeating steps (c) and (d) three or more times in succession, to produce selected higher generation backcross progeny plants that express the desired trait.

18. The method of claim 17, additionally comprising the step of planting a plurality of rice seed produced by selecting higher generation backcross progeny plants under conditions favorable for the growth of rice plants and optionally comprising the step of producing rice seed from the resulting rice plants.

* * * * *